United States Patent [19]

Fabinski et al.

[11] 4,176,963
[45] Dec. 4, 1979

[54] DEVICE FOR DETERMINING THE NITROGEN OXIDE CONCENTRATION IN A GASEOUS MIXTURE

[75] Inventors: Walter Fabinski, Hattersheim; Reimar Faulhaber, Frankfurt am Main, both of Fed. Rep. of Germany

[73] Assignee: Hartman & Braun AG., Frankfurt am Main, Fed. Rep. of Germany

[21] Appl. No.: 740,307

[22] Filed: Nov. 9, 1976

[30] Foreign Application Priority Data

Nov. 28, 1975 [DE] Fed. Rep. of Germany ...... 2553565

[51] Int. Cl.² .................. G01J 3/48; G01N 21/22; G01J 3/46
[52] U.S. Cl. .................. 356/418; 356/435; 356/408; 356/425; 250/345
[58] Field of Search .............. 250/339, 345, 350, 340; 356/188, 51, 206, 195, 179, 88

[56] References Cited

U.S. PATENT DOCUMENTS

| | | | |
|---|---|---|---|
| 2,939,361 | 6/1960 | Hock | 356/206 |
| 3,689,158 | 9/1972 | Shifrin | 356/88 |
| 3,793,525 | 2/1974 | Burch et al. | 250/343 |
| 3,811,776 | 5/1974 | Blau | 351/51 |
| 3,861,809 | 1/1975 | Hall | 356/188 |
| 3,947,685 | 3/1976 | Meinel | 250/345 |
| 4,008,394 | 2/1977 | Risgin et al. | 250/345 |
| 4,053,236 | 10/1977 | Atwood et al. | 356/206 |

*Primary Examiner*—Vincent P. McGraw
*Assistant Examiner*—Rodney B. Bovernick
*Attorney, Agent, or Firm*—Smyth, Pavitt, Siegemund, Jones & Martella

[57] ABSTRACT

Apparatus for determining the nitrogen oxide concentration in a gaseous mixture while minimizing measuring errors. The radiation from a hollow cathode lamp emitting the nitrogen oxide resonance radiation is modulated by a device for generating alternatively an unfiltered or test beam and a reference beam. The reference beam is filtered by a nitrogen oxide filled filter. An absorption cell is disposed in the path of the reference beam. Further, a monochromator or filter is provided and a detector for receiving the radiation from the monochromator filter. A signal processing unit is coupled to the detector for forming electric signals corresponding to the signal from the unfiltered and the reference beam and for forming the quotient thereof. A ray splitter is disposed in the path of the two beams to provide a different beam path and an additional radiation detector is disposed in the additional path. The signal processing unit has additional means for forming the quotient of the two signals generated by the additional detector and which have not passed the absorption cell. This will then provide an additional quotient of the two available quotients thus minimizing the normally occurring errors.

5 Claims, 4 Drawing Figures

DEVICE FOR DETERMINING THE NITROGEN OXIDE CONCENTRATION IN A GASEOUS MIXTURE

BACKGROUND OF THE INVENTION

This invention relates generally to an apparatus for determining the nitrogen oxide concentration in a gaseous mixture.

Such an apparatus has been disclosed in the German published application No. 24 07 133, see also U.S. Pat. No. 3,947,685. When it is desired to measure small concentrations of nitrogen oxide corresponding to an absorption coefficient $A=0.1$ in an absorption cell it is found that the normal equation controlling this process must be modified. The normal equation is:

$$I_M/I_V = K(1-A) \qquad (1)$$

wherein $I_M$ is the test signal also called unfiltered signal, $I_V$ the reference signal, A the absorption and K a constant. The modified equation is as follows:

$$a(p,T,t)I_M/I_V = K(1-A) \qquad (2)$$

wherein p is the pressure in the discharge lamp, T the ambient temperature and t the time. The time t indicates that the test signal may drift with time which may, for example, be caused by aging effects. The disturbance factor alpha is typically between 0.95 and 1.05. Assuming that A is 0.1, $\alpha$ produces within the limits given a measured error of $\pm 50\%$ in the nitrogen oxide concentration.

In case a discharge lamp is used which is filled with an oxygen-nitrogen mixture (for example, air) of reduced pressure, a pressure change in the lamp may be caused, for example, by a change in the ambient temperature or be due to a slow gas clean-up in the lamp. This pressure change causes a change of the emission characteristics of the gas discharge lamp. The lamp emits two fractions, one fraction being caused by NO molecules, the state of which corresponds to an occupation probability temperature of about 300° K. (Kelvin) and another portion corresponding to an occupation probability temperature of about 1500° K. Because the ratio of the two fractions depends on the gas pressure the observed measuring error is primarily due to this change.

Similar conditions prevail in the modulating device when a filter cell filled with NO gas is utilized. Finally the monochromator or an interference filter used instead is subject to aging and has a certain temperature dependence. This also causes errors of the final measuring result. These influences are combined in the disturbance factor alpha.

It is accordingly an object of the present invention to minimize or eliminate the influence of this disturbance factor in the region of low NO concentrations upon the final measuring result.

SUMMARY OF THE INVENTION

A discharge lamp containing a gas is used to generate a beam of radiant energy known to include certain spectral characteristics unique to the gas used.

A filter cell containing the same gas is alternately interposed in and removed from the beam of radiant energy. This periodically attenuates the unique spectral characteristics by absorption. The beam is then passed through a spectral filter which passes only radiation having the unique spectral characteristics. Thereafter, the beam is passed through a beam splitter which directs a fraction of the beam to a first detector.

With the filter in the beam, the intensity of this fraction of the beam is sensed by the first detector and converted to a current $I_{M'}$. With the filter removed from the beam, the intensity of the beam is again sensed and converted to a current $I_{V'}$.

The remainder of the beam is passed by the beam splitter to an absorption cell which includes an unknown amount of the same gas. The amount is determined from the fractional absorption of the beam as a result of its passage through the absorption cell.

With the filter cell removed from the beam, the intensity of radiation passing through the absorption cell is sensed by a second detector which converts the intensity to a current $I_V$. With the filter cell interposed in the beam the intensity of the radiation passing through the absorption cell is again sensed and converted to a current $I_M$.

The ratio of the intensities corresponding to $I_{M'}$ and $I_{V'}$ is influenced by a number of ambient conditions such as pressure, temperature, and time. The inputs to the absorption cell are in the same ratio and are influenced in the same way by the same variables. Thus, one would expect the ratio of the outputs of the absorption cell to be similarly influenced. In addition, that ratio, $I_M/I_V$, is proportional to $(1-A)$ where A is the fractional absorption. Therefore, when $I_M/I_V$ is arrived by $I_{M'}/I_{V'}$, the factor representing the influence of the ambient conditions cancels out, leaving only the absorption term $(1-A)$, from which the gas concentration can be determined.

Thus, the influence of the ambient conditions is cancelled out by the double measurement technique embodied in the present invention. As a result, greater accuracy is obtained because unpredictable variations in the ambient conditions cannot affect the results obtained.

BRIEF DESCRIPTION OF THE DRAWINGS

While the specification concludes with claims particularly pointing out and distinctly claiming the subject matter which is regarded as the invention, it is believed that the invention, the objects and features of the invention and further objects, features and advantages thereof will be better understood from the following description taken in connection with the accompanying drawings in which:

DESCRIPTION OF THE PREFERRED EMBODIMENTS

Figure 1:
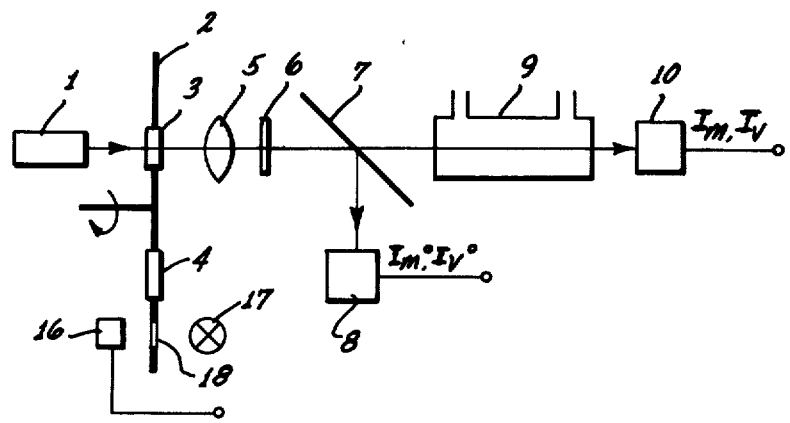
FIG. 1 is a schematic representation of a first embodiment of the invention.

Referring now to FIG. 1, there is illustrated a hollow cathode or discharge lamp 1 which is operated with an oxygen-nitrogen mixture (for example, air) at reduced pressure and at a low discharge current. Accordingly the lamp 1 emits the nitrogen oxide resonance radiation. This radiation is modulated by a rotating disk 2 containing two filter cells 3 and 4. Filter cell 3 is filled with nitrogen oxide which preferably has a pressure of one atmosphere and which accordingly absorbs a portion of the radiation when the cell is interposed into the radiation. On the other hand, the radiation is not influenced when the cell 4 enters the path of the radiation because the cell 4 is filled with air. The walls of the filter cells consist of a material transparent within the spectral region of the radiation.

A lens 5 generates a parallel beam of the two radiation portions which periodically follow each other and which are respectively filtered and unfiltered. These beam portions after having passed an interference filter 6 or monochromator pass a ray splitter 7. This ray splitter 7 is a semi-transparent mirror by means of which a portion of the radiation is diverted into the radiation receiver or detector 8. The portion of the radiation not diverted passes in the usual manner through an absorption cell 9 which is filled with the gas to be measured and containing nitrogen oxide. Subsequently the radiation is received by a radiation receiver or detector 10.

The detector 8 such, for example, as a photomultiplier generates periodically two signals $I_{M^*}$ and $I_{V^*}$. The two signals $I_M$ and $I_V$ generated by the detector 10 are further modified with respect to the filtered and unfiltered radiation by their absorption in the absorption cell 9. The signals $I_V$ and $I_{V^*}$ like the signals $I_M$ and $I_{M^*}$, are generated simultaneously. The index M is meant to indicate that the signal is generated by that portion of the radiation which is not influenced by the filter cell 3 of the modulation device (the test beam); the index V relates to a signal oriented from the filtered radiation (reference beam). The index* indicates that the radiation and accordingly the signal are not influenced by the gas mixture in the absorption cell 9. Accordingly, from the equation (2) the following equation is obtained.

$$a(p,T,t)I_{M^*}/I_{V^*} = K \qquad (3)$$

From the equations (2) and (3) the following equation can now be derived:

$$(I_{V^*}/I_{M^*})\times(I_M/I_V) = (1-A) \qquad (4)$$

The only unknown in equation (4) is the absorption A of the nitrogen oxide resonance radiation in the test cell 9 corresponding to the portion of the nitrogen oxide in the gas mixture to be measured. One can now electrically solve the equation (4) from the four signals $I_M$, $I_V$, $I_{M^*}$ and $I_{V^*}$. The signal which is obtained does not depend upon the disturbance factor $a$ and this signal corresponds to A and hence to the nitrogen oxide concentration in accordance with equation (5).

$$A = (I_V/I_{V^*} - I_M/I_{M^*})/I_V/I_{V^*} \qquad (5)$$

This equation could also be written as:

$$A = 1 - \frac{I_M}{I_V} \cdot \frac{I_{V^*}}{I_{M^*}} \text{ or,}$$

still alternatively:

$$A = (I_{V^*}I_{M^*} - I_M I_{V^*})/I_{V^*}I_{M^*}$$

Figure 3:
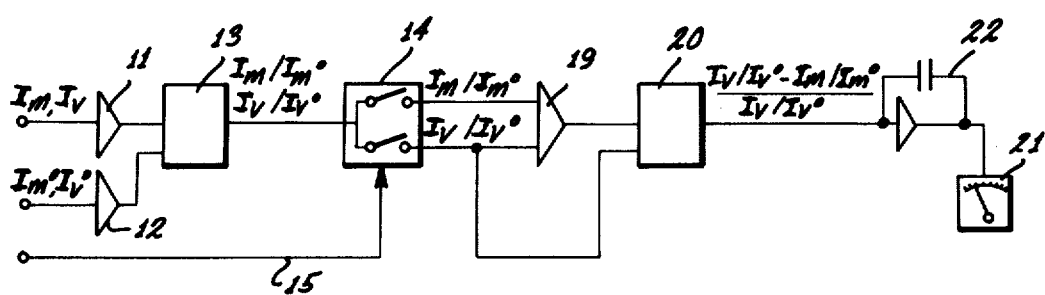
FIG. 3 is a schematic block diagram of a signal processing unit utilized in accordance with the invention in connection with the embodiments of FIGS. 1 and 2.

FIG. 3 to which reference is now made illustrates in block form a circuit diagram of the signal processing unit to solve directly equation (5). The signals generated by the two detectors 8 and 10 are amplified by amplifiers 11 and 12. These alternating pairs of signals, $I_M$, $I_{M^*}$, and $I_V$, $I_{V^*}$, are fed to a divider 13 which now forms the two quotients $I_M/I_{M^*}$ and $I_V/I_{V^*}$. These quotient signals periodically follow each other and are fed to an electronic switch 14. The switch 14 transfers the two quotients on separate leads by means of a control signal received on the lead 15, the control signal being dependent on the rotation of disk 2. The synchronous control signal is obtained in a known manner by a photocell 16 cooperating with a lamp 17, the radiation of which falls through an aperture 18 in the disk 2 upon the photocell 16 as shown in FIG. 1.

By means of a circuit such as a differential amplifier 19 and a further divider 20 the value of equation (5) is obtained. The indicator 21 shows the value A and a low pass filter 22 may be inserted ahead of the meter 21 to smooth out the signal.

It will be evident that equation (4) may also be modified in other ways. Accordingly it is possible to provide different signal processing units for measuring the quantity A.

Figure 2:
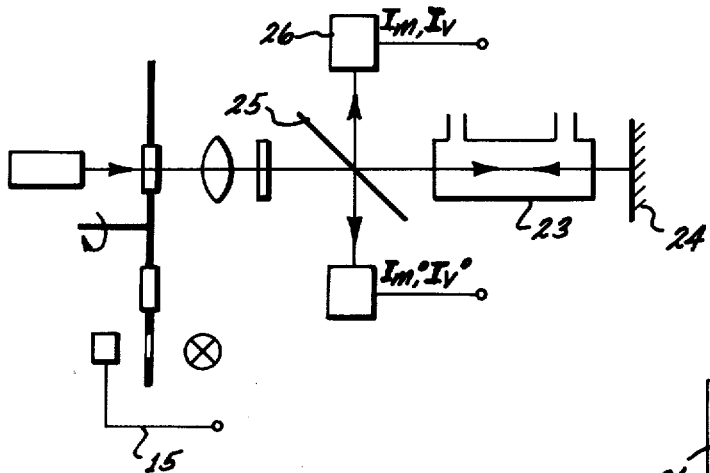
FIG. 2 is a schematic diagram of a modified embodiment of the invention.

Referring now to FIG. 2, there is illustrated a modified apparatus where the absorption cell 23 is passed twice by the radiation or the beams by providing a reflector 24. The partially transparent mirror 25 passes the reflected test and reference ray into the detector 26 which then generates periodic signals corresponding to $I_M$ and $I_V$. Otherwise the apparatus of FIG. 2 corresponds to that of FIG. 1.

Figure 4:
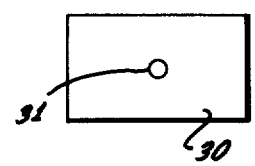
FIG. 4 is an elevational view of a mirror with a central opening which may be used as a ray splitter in accordance with the invention.

Instead of utilizing a partially transparent mirror as a ray splitter, it is also feasible to utilize a quartz plate 7 or 25. Alternatively as shown in FIG. 4, a mirror 30 may be used having a central opening 31.

It is also feasible to measure other gases such, for example, as $SO_2$. The same apparatus may be used because the hollow cathode lamp generates a radiation spectrum having a wavelength region which is also suitable for the absorption characteristics of other gases.

The invention is not limited to the embodiments described above but all changes and modifications thereof not constituting departures from the spirit and scope of the invention are intended to be included.

We claim:

1. An apparatus for determining the nitrogen-oxide concentration in a gaseous mixture;
under utilization of (a) a hollow cathode lamp operated with an oxygen-nitrogen mixture at reduced pressure and at a low discharge current and capable of emitting the nitrogen oxide resonance radiation;

(b) a radiation modulating device for generating/alternatingly an unfiltered beam to be measured and a reference beam;

(c) a nitrogen-oxide filter for filtering said reference beam; and (d) an absorption cell filled with the gas mixture to be measured and disposed in the path of said reference and said unfiltered beam; the improvement for minimizing measuring errors due to variations in the operation of the lamp comprising:
a monochromator or filter disposed between said filter and said cell;
a first detector for receiving radiation of said alternating beams and having passed through said cell;
first signal processing means connected to said detector for acquiring two alternating detector signals corresponding to the unfiltered beam and the reference beam, both having passed through said absorption cell;

a ray splitter disposed in the path of said beams ahead of said cell to provide a second, different beam path but permitting some radiation to reach the first detector;

a second radiation detector disposed in said additional path;

second signal processing means connected to the second detector for acquiring alternately two detector signals corresponding also to the unfiltered beam and the reference beam but which have not passed the absorption cell; and third signal processing means connected to said first and second signal processing means for arithmetically combining said four detector signals to obtain a signal indicative of absorption by the absorption cell, under elimination of variations in a ratio between unfiltered and reference beam on account of variations in the operation of said lamp.

2. Apparatus as defined in claim 1 wherein said ray splitter is a partially transparent mirror.

3. Apparatus as defined in claim 1 wherein said ray splitter is a quartz plate.

4. Apparatus as claimed in claim 1 wherein said ray splitter is a mirror having a small central opening.

5. Apparatus as defined in claim 1 wherein a reflector is provided associated with said absorption cell for causing the rays to pass twice through said cell.

* * * * *